(12) United States Patent
Ali et al.

(10) Patent No.: US 9,062,116 B2
(45) Date of Patent: Jun. 23, 2015

(54) ANTI-FATTY ACID AMIDE HYDROLASE-2 ANTIBODIES AND USES THEREOF

(75) Inventors: Janid A. Ali, Cambridge, MA (US); James Brownell, Winchester, MA (US); Erin Brophy, Dover, NH (US); Thomas T. Tibbitts, Westford, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 829 days.

(21) Appl. No.: 13/265,330

(22) PCT Filed: Apr. 22, 2010

(86) PCT No.: PCT/US2010/032087
§ 371 (c)(1),
(2), (4) Date: Jan. 5, 2012

(87) PCT Pub. No.: WO2010/124113
PCT Pub. Date: Oct. 28, 2010

(65) Prior Publication Data
US 2012/0115162 A1 May 10, 2012

Related U.S. Application Data

(60) Provisional application No. 61/171,938, filed on Apr. 23, 2009.

(51) Int. Cl.
*G01N 33/53* (2006.01)
*G01N 31/00* (2006.01)
*C07K 16/40* (2006.01)

(52) U.S. Cl.
CPC ..................... *C07K 16/40* (2013.01)

(58) Field of Classification Search
CPC ........... C12Q 1/6886; C12Q 2600/158; G01N 33/574; G01N 33/57407
See application file for complete search history.

(56) References Cited

U.S. PATENT DOCUMENTS

| | | |
|---|---|---|
| 4,399,216 A | 8/1983 | Axel et al. |
| 4,634,655 A | 1/1987 | Yanagimoto et al. |
| 4,816,567 A | 3/1989 | Cabilly et al. |
| 5,179,017 A | 1/1993 | Axel et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,476,996 A | 12/1995 | Wilson et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,260 A | 7/1997 | Winter et al. |
| 5,661,016 A | 8/1997 | Lonberg et al. |
| 5,677,425 A | 10/1997 | Bodmer et al. |
| 5,693,762 A | 12/1997 | Queen et al. |
| 5,698,767 A | 12/1997 | Wilson et al. |
| 5,714,350 A | 2/1998 | Co et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,033,862 A | 3/2000 | Matsuda et al. |
| 6,075,181 A | 6/2000 | Kucherlapati et al. |
| 6,096,784 A | 8/2000 | Lerner et al. |
| 6,114,598 A | 9/2000 | Kucherlapati et al. |
| 6,121,022 A | 9/2000 | Presta et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,172,197 B1 | 1/2001 | McCafferty et al. |
| 6,180,370 B1 | 1/2001 | Queen et al. |
| 6,194,551 B1 | 2/2001 | Idusogie et al. |
| 6,271,015 B1 | 8/2001 | Gilula et al. |
| 6,277,375 B1 | 8/2001 | Ward |
| 6,350,861 B1 | 2/2002 | Co et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |

(Continued)

FOREIGN PATENT DOCUMENTS

| | | |
|---|---|---|
| EP | 338841 | 10/1989 |
| EP | 0440082 | 8/1991 |

(Continued)

OTHER PUBLICATIONS

Bird et al., "Single-chain antigen-binding proteins," Science 242(4877):423-426 (1988).
Boss and Wood, "Genetically engineered antibodies," Immunology Today 6:12-13 (1985).
Bracey et al., "Structural Adaptations in Membrane Enzyme That Terminates Endocannabinoid Signaling," Science 298:1793-1796 (2002).
Chen et al., "B cell development in mice that lack one or both immunoglobulin kappa light chain genes," EMBO J. 12(3):821-830 (1993).

(Continued)

*Primary Examiner* — Lisa Cook
(74) *Attorney, Agent, or Firm* — Jones Day

(57) ABSTRACT

Antibodies that specifically bind to fatty acid amide hydrolases and methods of using the antibodies are provided herein.

21 Claims, No Drawings

(56) References Cited

U.S. PATENT DOCUMENTS

| | | | |
|---|---|---|---|
| 6,582,915 | B1 | 6/2003 | Griffiths et al. |
| 6,593,081 | B1 | 7/2003 | Griffiths et al. |
| 6,703,199 | B1 | 3/2004 | Koide |
| 6,869,046 | B2 | 3/2005 | McEvoy |
| 7,553,496 | B2 | 6/2009 | Ambati |
| 2002/0164769 | A1 | 11/2002 | Curtis et al. |
| 2003/0153043 | A1 | 8/2003 | Carr et al. |

FOREIGN PATENT DOCUMENTS

| | | |
|---|---|---|
| WO | WO 8704462 | 7/1987 |
| WO | WO 8901036 | 2/1989 |
| WO | WO 9312227 | 6/1993 |
| WO | WO 9425585 | 11/1994 |
| WO | WO 9429351 | 12/1994 |
| WO | WO 9824396 | 6/1998 |
| WO | WO 9824884 | 6/1998 |
| WO | WO 9945962 | 9/1999 |
| WO | WO 0042072 | 7/2000 |
| WO | WO 0114424 | 3/2001 |
| WO | WO 0243478 | 6/2002 |
| WO | WO 02059155 | 8/2002 |
| WO | WO 2004044169 | 5/2004 |
| WO | WO 2008047229 | 4/2008 |
| WO | WO 2008063300 | 5/2008 |
| WO | WO 2009011904 | 1/2009 |
| WO | WO 2009126691 | 2/2010 |

OTHER PUBLICATIONS

Chen et al., "Immunoglobulin gene rearrangement in B cell deficient mice generated by targeted deletion of the JH locus," Int. Immunol. 5(6):647-656 (1993).

Choi et al., "Transgenic mice containing a human heavy chain immunoglobulin gene fragment cloned in a yeast artificial chromosome," Nat. Genet. 4(2):117-123 (1993).

Cox et al., "A directory of human germ-line V kappa segments reveals a strong bias in their usage," Eur. J. lmmunol. 24(4):827-836 (1994).

Cravatt et al., "Functional disassociation of the central and peripheral fatty acid amide signaling systems," Proc. Natl. Acad. Sci. U.S.A. 101(29):10821-10826 (2004).

Cravatt et al., "Supersensitivity to Anandamide and Enhanced Endogenous Cannabinoid Signaling in Mice Lacking Fatty Acid Amide Hydrolase," Proc. Natl. Acad. Sci. U.S.A. 98:9371-9376 (2001).

Deutsch, "Design of On-Target FAAH Inhibitors," Chem. Biol. 12(11):1157-1158 (2005).

Drake et al., "Characterizing high-affinity antigen/antibody complexes by kinetic- and equilibrium-based methods," Anal. Biochem. 328(1):35-43 (2004).

Fishwild et al., "High-avidity human IgG kappa monoclonal antibodies from a novel strain of minilocus transgenic mice," Nat. Biotechnol. 14(7):845-851 (1996).

Giang and Cravatt, "Molecular characterization of human and mouse fatty acid amide hydrolases," Proc. Natl. Acad. Sci. U.S.A. 94(6):2238-2242 (1997).

Harding and Lonberg, "Class switching in human immunoglobulin transgenic mice," Ann. N. Y. Acad. Sci. 764:536-546 (1995).

Hattis, "Use of biological markers and pharmacokinetics in human health risk assessment," Environ. Health Perspect. 90:229-238 (1991).

Hillard et al., "Characterization of the kinetics and distribution of N-arachidonylethanolamine (anandamide) hydrolysis by rat brain," Biochim. Biophys. Acta. 1257(3):249-256 (1995).

Holliger and Hudson, "Engineered antibody fragments and the rise of single domains," Nat. Biotechnol. 23(9):1126-1136 (2005).

Huang et al., "Identification of a new class of molecules, the arachidonyl amino acids, and characterization of one member that inhibits pain," J. Biol. Chem. 276(46):42639-42644 (2001).

Huston et al., "Protein engineering of antibody binding sites: recovery of specific activity in an anti-digoxin single-chain Fv analogue produced in Escherichia coli," Proc. Natl. Acad. Sci. U. S. A. 85(16):5879-5883 (1988).

Jones et al., "Replacing the complementarity-determining regions in a human antibody with those from a mouse," Nature 321(6069):522-525 (1986).

Karbarz et al., "Biochemical and biological properties of 4-(3-phenyl-[1,2,4] thiadiazol-5-yl)- piperazine-1-carboxylic acid phenylamide, a mechanism-based inhibitor of fatty acid amide hydrolase," Anesth. Analg. 108(1):316-329 (2009).

Kathuria et al., "Modulation of anxiety through blockade of anandamide hydrolysis," Nat. Med. 9(1):76-81 (2003).

Kaufman and Sharp, "Amplification and expression of sequences cotransfected with a modular dihydrofolate reductase complementary dna gene," J. Mol. Biol. 159(4):601-621 (1982).

Köhler and Milstein, "Continuous cultures of used cells secreting antibody of predefined specificity," Nature 256(5517):495-497 (1975).

Koomen et al., "Mapping of surrogate markers of cellular components and structures using laser desorption/ionization mass spectrometry," J. Mass. Spectrom.35(2):258-264 (2000).

Kuroiwa et al., "Cloned transchromosomic calves producing human immunoglobulin," Nat. Biotechnol. 20(9):889-894 (2002).

Labar et al., "Fatty Acid Amide Hydrolase: From Characterization to Therapeutics," Chem. Biodivers. 4(8):1882-1902 (2007).

Lambert and Fowler, "The endocannabinoid system: Drug targets, lead compounds, and potential therapeutic applications," J. Med. Chem. 48(16):5059-5087 (2005).

Lonberg and Huszar, "Human antibodies from transgenic mice," Int. Rev. Immunol. 13(1):65-93 (1995).

Lonberg et al., "Antigen-specific human antibodies from mice comprising four distinct genetic modifications," Nature 368(6474):856-859 (1994).

Maurelli et al, "Two novel classes of neuroactive fatty acid amides are substrates for mouse neuroblastoma 'anandamide amidohydrolase'," FEBS Lett. 377(1):82-86 (1995).

McCafferty et al., "Phage antibodies: filamentous phage displaying antibody variable domains," Nature 348(6301):552-554 (1990).

McKinney et al., "Structure and Function of Fatty Acid Amide Hydrolase," Ann. Rev. Biochem. 74:411-432 (2005).

McPartland et al, "A shifted repertoire of endocannabinoid genes in the zebrafish (Danio rerio)," Mol. Genet. Genomics 277:555-570m (2007).

Mendelson and Basile, "The Hypnotic Actions of the Fatty Acid Amide, Oleamide," Neuropsychopharmacology 25(5 Suppl):S36-S39 (2001).

Minkkila et al., "Discovery of Boronic Acids as Novel and Potent Inhibitors of Fatty Acid Amide Hydrolase," J. Med. Chem. 51:7057-7060 (2008).

Morrison, "Transfectomas provide novel chimeric antibodies," Science 229(4719):1202-1207 (1985).

Nicolau, "Using pharmacodynamic and pharmacokinetic surrogate markers in clinical practice: optimizing antimicrobial therapy in respiratory-tract infections," Am. J. Health Syst. Pharm. 56(22 Suppl 3):S16-S20 (1999).

Nygren and Uhlén, "Scaffolds for engineering novel binding sites in proteins," Curr. Opin. Struct. Biol. 7(4):463-469 (1997).

Pacher et al., "The endocannabinoid system as an emerging target of pharmacotherapy," Pharmacol. Rev. 58(3):389-462 (2006).

Patricelli et al., "Comparative characterization of a wild type and transmembrane domain-deleted fatty acid amide hydrolase: identification of the transmembrane domain as a site for oligomerization," Biochemistry 37(43):15177-15187 (1998).

Pillarisetti et al., "Pain and beyond: fatty acide amides and fatty acide amide hydrolase inhibitors in cardiovascular and metabolic diseases," Drug Discov. 1-14 (2009).

Piomelli et al., "Pharmacological Profile of the Selective FAAH Inhibitor KDS-4103 (URB597)," CNS Drug Rev. 12(1):21-38 (2006).

Queen et al., "A humanized antibody that binds to the interleukin 2 receptor," Proc. Natl. Acad. Sci. U. S. A. 86(24):10029-10033 (1989).

Quistad et al., "Fatty Acid Amide Hydrolase Inhibition by Neurotoxic Organophosphous Pesticides," Toxicol. Appl. Pharmacol. 173(1):48-55 (2001).

(56) References Cited

OTHER PUBLICATIONS

Ramarao et al., "A Fluorescence-Based Assay for Fatty Acid Amide Hydrolase Compatible with High-Throughput Screening," Anal. Biochem. 343:143-151 (2005).

Reichmann et al., "Reshaping Human Antibodies for Therapy," Nature 332(6162):323-327 (1988).

Saghetelian et al., "A FAAH-regulated class of N-acyl taurines that activates TRP ion channels," Biochemistry 45(30):9007-9015 (2006).

Schentag, "Pharmacokinetic and pharmacodynamic surrogate markers: studies with fluoroquinolones in patients," Am. J. Health Syst. Pharm. 56(22 Suppl 3):S21-S24 (1999).

Schlosburg et al., "Targeting Fatty Acide Amide Hydrolase (FAAH) to Treat Pain and Inflammation," The AAOS J. 11(1):39-44 (2009).

Shields et al., "High resolution mapping of the binding site on human IgG1 for FcγRI, FcγRII, FcγRIII, and FcRn and design of IgG1 variants with improved binding to the FcγR," J. Biol. Chem. 276(9):6591-6604 (2001).

Takebe et al., "SR alpha promoter: an efficient and versatile mammalian cDNA expression system composed of the simian virus 40 early promoter and the R-U5 segment of human T-cell leukemia virus type 1 long terminal repeat," Mol. Cell. Biol. 8(1):466-472 (1988).

Taylor et al., "A transgenic mouse that expresses a diversity of human sequence heavy and light chain immunoglobulins," Nucleic Acids Res. 20(23):6287-6295 (1992).

Taylor et al., "Human immunoglobulin transgenes undergo rearrangement, somatic mutation and class switching in mice that lack endogenous IgM," Int. Immunol. 6(4): 579-591 (1994).

Tomizuka et al., "Double trans-chromosomic mice: maintenance of two individual human chromosome fragments containing Ig heavy and ? loci and expression of fully human antibodies," Proc. Natl. Acad. Sci. U. S. A. 97(2):722-727 (2000).

Tomlinson et al., "The repertoire of human germline VH sequences reveals about fifty groups of VH segments with different hypervariable loops," J. Mol. Biol. 227(3):776-798 (1992).

Tuaillon et al. "Human immunoglobulin heavy-chain minilocus recombination in transgenic mice: Gene-segment use in ? and ? transcripts," Proc. Natl. Acad. Sci. U.S.A. 90(8):3720-3724 (1993).

Tuaillon et al., "Biased utilization of DHQ52 and JH4 gene segments in a human Ig transgenic minilocus is independent of antigenic selection," J. Immunol. 152(6):2912-2920 (1994).

Urlaub and Chasin, "Isolation of Chinese hamster cell mutants deficient in dihydrofolate reductase activity," Proc. Natl. Acad. Sci. U. S. A. 77(7):4216-4220 (1980).

Vandervoorde, "Overview of the Chemical Families of Fatty Acid Amide Hydrolase and Monoacylglycerol Lipase Inhibitors," Curr. Top. Med. Chem. 8(3):247-267 (2008).

Walker et al., "Pain modulation by release of the endogenous cannabinoid anandamide," Proc. Natl. Acad. Sci. U. S. A. 96(21):12198-12203 (1999).

Wang et al., "High-Throughput Screening for the Discovery of Inhibitors of Fatty Acid Amide Hydrolase Using a Microsome-Based Fluorescent Assay," J. Biomol. Screen. 11:519-527(2006).

Ward et al., "Binding activities of a repertoire of single immunoglobulin variable domains secreted from *Escherichia coli*," Nature 341(6242):544-546 (1989).

Wei et al., "A second fatty acid amide hydrolase with variable distribution among placental mammals," J. Biol. Chem. 281(48):36569-36578 (2006).

Zapata et al., "Engineering linear F(ab')2 fragments for efficient production in *Escherichia coli* and enhanced antiproliferative activity," Protein Eng. 8(10):1057-1062 (1995).

SEQUENCE LISTING

<160> NUMBER OF SEQ ID NOS: 4

<210> SEQ ID NO 1
<211> LENGTH: 532
<212> TYPE: PRT
<213> ORGANISM: Homo sapiens
<220> FEATURE:
<223> OTHER INFORMATION: human fatty acid amide hydrolase 2

<400> SEQUENCE: 1

```
Met Ala Pro Ser Phe Thr Ala Arg Ile Gln Leu Phe Leu Leu Arg Ala
 1               5                  10                  15

Leu Gly Phe Leu Ile Gly Leu Val Gly Arg Ala Ala Leu Val Leu Gly
                20                  25                  30

Gly Pro Lys Phe Ala Ser Lys Thr Pro Arg Pro Val Thr Glu Pro Leu
            35                  40                  45

Leu Leu Leu Ser Gly Met Gln Leu Ala Lys Leu Ile Arg Gln Arg Lys
50                  55                  60

Val Lys Cys Ile Asp Val Val Gln Ala Tyr Ile Asn Arg Ile Lys Asp
65                  70                  75                  80

Val Asn Pro Met Ile Asn Gly Ile Val Lys Tyr Arg Phe Glu Glu Ala
                85                  90                  95

Met Lys Glu Ala His Ala Val Asp Gln Lys Leu Ala Glu Lys Gln Glu
            100                 105                 110

Asp Glu Ala Thr Leu Glu Asn Lys Trp Pro Phe Leu Gly Val Pro Leu
        115                 120                 125

Thr Val Lys Glu Ala Phe Gln Leu Gln Gly Met Pro Asn Ser Ser Gly
    130                 135                 140

Leu Met Asn Arg Arg Asp Ala Ile Ala Lys Thr Asp Ala Thr Val Val
145                 150                 155                 160

Ala Leu Leu Lys Gly Ala Gly Ala Ile Pro Leu Gly Ile Thr Asn Cys
                165                 170                 175

Ser Glu Leu Cys Met Trp Tyr Glu Ser Ser Asn Lys Ile Tyr Gly Arg
            180                 185                 190

Ser Asn Asn Pro Tyr Asp Leu Gln His Ile Val Gly Gly Ser Ser Gly
        195                 200                 205

Gly Glu Gly Cys Thr Leu Ala Ala Ala Cys Ser Val Ile Gly Val Gly
    210                 215                 220

Ser Asp Ile Gly Gly Ser Ile Arg Met Pro Ala Phe Phe Asn Gly Ile
225                 230                 235                 240

Phe Gly His Lys Pro Ser Pro Gly Val Val Pro Asn Lys Gly Gln Phe
                245                 250                 255

Pro Leu Ala Val Gly Ala Gln Glu Leu Phe Leu Cys Thr Gly Pro Met
            260                 265                 270

Cys Arg Tyr Ala Glu Asp Leu Ala Pro Met Leu Lys Val Met Ala Gly
        275                 280                 285

Pro Gly Ile Lys Arg Leu Lys Leu Asp Thr Lys Val His Leu Lys Asp
    290                 295                 300

Leu Lys Phe Tyr Trp Met Glu His Asp Gly Gly Ser Phe Leu Met Ser
305                 310                 315                 320

Lys Val Asp Gln Asp Leu Ile Met Thr Gln Lys Val Val His
                325                 330                 335

Leu Glu Thr Ile Leu Gly Ala Ser Val Gln His Val Lys Leu Lys Lys
            340                 345                 350

Met Lys Tyr Ser Phe Gln Leu Trp Ile Ala Met Met Ser Ala Lys Gly
```

```
                   355                 360                 365
His Asp Gly Lys Glu Pro Val Lys Phe Val Asp Leu Leu Gly Asp His
    370                 375                 380

Gly Lys His Val Ser Pro Leu Trp Glu Leu Ile Lys Trp Cys Leu Gly
385                 390                 395                 400

Leu Ser Val Tyr Thr Ile Pro Ser Ile Gly Leu Ala Leu Leu Glu Glu
                405                 410                 415

Lys Leu Arg Tyr Ser Asn Glu Lys Tyr Gln Lys Phe Lys Ala Val Glu
            420                 425                 430

Glu Ser Leu Arg Lys Glu Leu Val Asp Met Leu Gly Asp Asp Gly Val
        435                 440                 445

Phe Leu Tyr Pro Ser His Pro Thr Val Ala Pro Lys His His Val Pro
    450                 455                 460

Leu Thr Arg Pro Phe Asn Phe Ala Tyr Thr Gly Val Phe Ser Ala Leu
465                 470                 475                 480

Gly Leu Pro Val Thr Gln Cys Pro Leu Gly Leu Asn Ala Lys Gly Leu
                485                 490                 495

Pro Leu Gly Ile Gln Val Val Ala Gly Pro Phe Asn Asp His Leu Thr
            500                 505                 510

Leu Ala Val Ala Gln Tyr Leu Glu Lys Thr Phe Gly Gly Trp Val Cys
        515                 520                 525

Pro Gly Lys Phe
    530

<210> SEQ ID NO 2
<211> LENGTH: 2039
<212> TYPE: DNA
<213> ORGANISM: Homo sapiens
<220> FEATURE:
<223> OTHER INFORMATION: human fatty acid amide hydrolase 2

<400> SEQUENCE: 2
gataaacaag ctcctgtgga attgtgggta gacactggac ttgtaaacga aaagcttcat      60
aagtccctct ttgcttagta cttttctcgt cctttcccca gggtgcacgt aaccctcaag     120
cactaggacc gtgcggaatc caggctgcga tggcaccttc atttaccgcc cgcattcagt     180
tgttcctctt gcgggcgcta ggctttctca taggcttagt aggccgagca gctttagtct     240
tagggggtcc aaagtttgcc tcaaagaccc ctcggccggt gactgaacca ttgcttctgc     300
tttcggggat gcagctggcc aagctgatcc gacagagaaa ggtgaaatgt atagatgttg     360
ttcaggctta tatcaacaga atcaaggacg tgaacccaat gatcaatgga attgtcaagt     420
acaggtttga ggaagcgatg aaggaggctc atgctgtaga tcaaaagctt gcagagaagc     480
aggaagatga agccaccctg gaaaataaat ggcccttcct tggggttcct ttgacagtca     540
aggaagcttt ccagctacaa ggaatgccca attcttctgg actcatgaac cgtcgtgatg     600
ccattgccaa aacagatgcc actgtggtgg cattactgaa gggagctggt gccattcctc     660
ttggcataac caactgtagt gagttgtgta tgtggtatga atccagtaac aagatctatg     720
gccgatcaaa caacccatat gatttacagc atattgtagg tggaagttct ggtggtgagg     780
gctgcacact ggcagctgcc tgctcagtta ttggtgtggg ctctgatatt ggtggtagca     840
ttcgaatgcc tgcttttctt aatggtatat ttggacacaa gccttctcca ggtgtggttc     900
ccaacaaagg tcagtttccc ttggctgtgg gagcccagga gttgtttctg tgcactggtc     960
ctatgtgccg ttatgctgaa gacctggccc ccatgttgaa ggtcatggca ggacctggga    1020
```

```
tcaaaaggtt aaaactagac acaaaggtac atttaaaaga cttaaaattt tactggatgg    1080
aacatgatgg aggctcattt ttaatgtcca aagtggacca agatctcatt atgactcaga    1140
aaaaggttgt ggttcacctt gaaactattc taggagcctc agttcaacat gttaaactga    1200
agaaaatgaa gtactctttt cagttgtgga tcgcaatgat gtcagcaaag ggacatgatg    1260
ggaaggaacc tgtgaaattt gtagatttgc ttggtgacca tgggaaacat gtcagtcctc    1320
tgtgggagtt gatcaaatgg tgcctgggtc tgtcagtgta caccatccct tccattggac    1380
tggctttgtt ggaagaaaag ctcagatata gcaatgagaa ataccaaaag tttaaggcag    1440
tggaagaaag cctgcgtaaa gagctggtgg atatgctagg tgatgatggt gtgttcttat    1500
atccctcaca tcccacagtg gcacctaagc atcatgtccc tctaacacgg cctttcaact    1560
ttgcttacac aggtgtcttc agtgccctgg gtttgcctgt gacccaatgc ccactgggac    1620
tgaatgccaa aggactccct ttaggcatcc aggttgtggc tggacccttt aatgatcatc    1680
tgaccctggc tgtggcccag tacttggaga aaacttttgg gggctgggtc tgtccaggaa    1740
agttttagga ggaccttctg caaggttaat gtgtgtgtgt gtttgtgttc gtgtggtggt    1800
gtttctatta attgggtgaa atcaagcacc agcagacaag cagagaaaca actggggaat    1860
ttattgactc atttagttat tctttctact tttatttcct tctctaactg ttggtcttac    1920
taaaatggta atatttgctt cttgctttta tgttactgga aaattaggac atgtaaatgg    1980
ataagtgcaa taaagtttcc taaatgctgg aaaaaaaaaa aaaaaaaaaa aaaaaaaa     2039
```

```
<210> SEQ ID NO 3
<211> LENGTH: 24
<212> TYPE: PRT
<213> ORGANISM: Homo sapiens
<220> FEATURE:
<223> OTHER INFORMATION: amino acids 414-437 of human fatty acid amide
      hydrolase 2

<400> SEQUENCE: 3

Leu Glu Glu Lys Leu Arg Tyr Ser Asn Glu Lys Tyr Gln Lys Phe Lys
1               5                   10                  15

Ala Val Glu Glu Ser Leu Arg Lys
            20

<210> SEQ ID NO 4
<211> LENGTH: 25
<212> TYPE: PRT
<213> ORGANISM: Artificial Sequence
<220> FEATURE:
<223> OTHER INFORMATION: synthetic antigenic epitope

<400> SEQUENCE: 4

Cys Leu Glu Glu Lys Leu Arg Tyr Ser Asn Glu Lys Tyr Gln Lys Phe
1               5                   10                  15

Lys Ala Val Glu Glu Ser Leu Arg Lys
            20                  25
```

US 9,062,116 B2

ANTI-FATTY ACID AMIDE HYDROLASE-2 ANTIBODIES AND USES THEREOF

CROSS-REFERENCE TO RELATED APPLICATIONS

The present application is the national phase entry pursuant to 35 U.S.C. §371 of International Application No. PCT/US2010/032087, which has an international filing date of Apr. 22, 2010, and which claims priority to U.S. provisional patent application Ser. No. 61/171,938, filed Apr. 23, 2009. The entire contents of the prior applications are herein incorporated by reference.

The present specification is being filed with a computer readable form (CRF) copy of the Sequence Listing. The CRF entitled SEQLIST_12928-008-999.TXT, which was created on Jan. 5, 2012 and is 8,044 bytes in size, is identical to the paper copy of the Sequence Listing and is incorporated herein by reference in its entirety.

BACKGROUND OF THE INVENTION

Fatty acid amides are biologically active lipids that mediate signaling associated with diverse processes such as sleep, pain, memory, and feeding. Classes of biologically active endogenous fatty acid amides include N-acylethanolamines (e.g., anandamide), N-acyl amino acids (e.g., N-acyl taurine), and fatty acid primary amides (e.g., oleamide). Anandamide activates cannabinoid receptors and elevated anandamide levels are observed in pain-sensitive areas of the brain in response to pain stimulation (Walter et al., 1999 Proc Natl Acad Sci USA. 96(21): 12198-12203). N-acyl amino acids have been shown to suppress pain and activate signaling through transient receptor potential (TRP) calcium channels (Huang et al., 2001 276(46):42639-44; Saghatelian et al., 2006 Biochem. 45(30):9007-15). Oleamide accumulates in the cerebrospinal fluid of sleep deprived animals, and administration of exogenous oleamide has sleep-inducing effects (Mendelson and Basile, 2001 Neuropsychopharmacol. 25(S5):S36-S39).

The biological activity of fatty acid amides is regulated by hydrolysis in vivo. Fatty acid amide hydrolase 1 (also known as FAAH or FAAH1) hydrolyzes N-acyl ethanolamines such as anandamide and N-acyl taurines Inhibition or complete disruption of FAAH1 signaling in rodents leads to elevated levels of endogenous fatty acid amides and correlates with reduced sensitivity to pain, and benzodiazepine-like anti-anxiety behaviors (Cravatt et al., 2001 Proc. Natl. Acad. Sci. U.S.A. 98(16): 9371-6; Kathuria et al., 2003 Nat. Med. 9(1): 76-81). Primates, marsupials, and other species have a gene encoding a second fatty acid amide hydrolase, FAAH2 (Wei et al., 2006 J. Biol. Chem. 281(48):36569-36578). FAAH2 and FAAH1 have distinct but overlapping substrate specificities. While both enzymes hydrolyze fatty acid amides, FAAH2 exhibits a preference for mono-unsaturated acyl chains whereas FAAH1 prefers polyunsaturated acyl chains. FAAH2 hydrolyzes anandamide at a ~50 fold lower rate than FAAH1. Both enzymes hydrolyze oleamide at an equivalent rate, and both enzymes are susceptible to inhibition by URB597, a carbamate inhibitor, and OL-135, an α-ketoheterocycle.

SUMMARY OF THE INVENTION

The present disclosure provides, inter alia, novel epitopes of FAAH2, antibodies that bind to FAAH2, methods of using anti-FAAH2 antibodies, and methods of producing anti-FAAH2 antibodies. Accordingly, in one aspect, the present disclosure provides an isolated antibody that specifically binds to an FAAH2. In some embodiments, an antibody binds to an epitope within a C-terminal region of an FAAH2, e.g., an epitope located C-terminal of the amidase signature domain, e.g., C-terminal of ~ amino acid 246 of SEQ ID NO:1. In some embodiments, an antibody binds to an epitope within or overlapping amino acids 246-532 of SEQ ID NO:1 (e.g., an epitope within or overlapping amino acids 246-437, 284-437, 300-437, 330-437, 360-437, 390-437, 330-532, 360-532, 390-532, 330-489, 330-476, 330-446, or 414-437 of SEQ ID NO:1). In some embodiments, an antibody binds to an epitope within or overlapping amino acids 414-437 of SEQ ID NO:1 (i.e., an epitope within or overlapping the following amino acid sequence: LEEKLRYSNEKYQK-FKAVEESLRK (SEQ ID NO:3)). In some embodiments, an antibody binds to an epitope within or overlapping amino acids 414-430 of SEQ ID NO:1. In some embodiments, an antibody binds to an epitope within or overlapping amino acids 414-425 of SEQ ID NO:1. In some embodiments, an antibody binds to an epitope within or overlapping amino acids 420-430 of SEQ ID NO:1.

In some embodiments, an anti-FAAH2 antibody specifically binds to human FAAH2, and is cross reactive with FAAH2 of a non-human species. In other embodiments, an anti-FAAH2 antibody specifically binds to human FAAH2 and does not cross-react with FAAH2 of a non-human species. In some embodiments, an anti-FAAH2 antibody is not cross-reactive with an FAAH1.

In some embodiments, an anti-FAAH2 antibody binds to a linear epitope of FAAH2. In some embodiments, an antibody binds to a non-linear epitope of FAAH2. In some embodiments, an antibody binds to an FAAH2 with a dissociation constant ($K_D$) equal to or less than 1 nM (e.g., a $K_D$ equal to or less than 0.5 nM. or 0.1 nM).

An anti-FAAH2 antibody as provided herein can be a monoclonal antibody or a polyclonal antibody (e.g., a polyclonal antibody produced in a rabbit, mouse, hamster, guinea pig, rat, goat, chicken, sheep, or horse). In some embodiments, an antibody is a human antibody. In some embodiments, an antibody is a humanized monoclonal antibody. An antibody can be an antibody of any isotype (e.g., IgM, IgG1, IgG2, IgG3, IgG4, IgA, IgE).

In some embodiments, an anti-FAAH2 antibody comprises an intact antibody. In some embodiments, an antibody comprises an Fab fragment, an Fab' fragment, an F(ab')$_2$, an Fv fragment, single chain Fv, or a diabody. In some embodiments, an anti-FAAH2 antibody is a chimeric antibody.

An anti-FAAH2 antibody provided herein can be an antibody that modulates an activity of FAAH2. For example, in some embodiments, an antibody modulates (e.g., inhibits) FAAH2 binding to an FAAH2 ligand. In some embodiments, an antibody modulates (e.g., inhibits) FAAH2 binding to a fatty acid (e.g., a mono-unsaturated fatty acid, e.g., oleamide). In some embodiments, an anti-FAAH2 antibody inhibits fatty acid amide hydrolase activity of FAAH2.

In some embodiments, an anti-FAAH2 antibody is labeled (e.g., with an enzyme, a fluorescent moiety, or a radioactive moiety).

The present disclosure also provides compositions and kits including an anti-FAAH2 antibody. In some embodiments, compositions and/or kits include an antibody that binds to an epitope within a C-terminal region of an FAAH2, e.g., an epitope located C-terminal of the amidase signature domain, e.g., C-terminal of ~ amino acid 246 of SEQ ID NO:1. In some embodiments, compositions and/or kits include an antibody that binds to an epitope within or overlapping amino acids 246-532 of SEQ ID NO:1 (e.g., an epitope within or overlapping amino acids 246-437, 284-437, 300-437, 330-437, 360-437, 390-437, 330-532, 360-532, 390-532, 330-489, 330-476, 330-446, or 414-437 of SEQ ID NO:1). In some embodiments, compositions and/or kits include an antibody that binds to an epitope within or overlapping amino acids 414-437 of SEQ ID NO:1 (i.e., an epitope within or overlapping the following amino acid sequence: LEEKLRYSNEKYQKFKAVEESLRK (SEQ ID NO:3)). In some embodiments, compositions and/or kits include an antibody that binds to an epitope within or overlapping amino acids 414-430 of SEQ ID NO:1. In some embodiments, compositions and/or kits include an antibody that binds to an epitope within or overlapping amino acids 414-425 of SEQ ID NO:1. In some embodiments, compositions and/or kits include an antibody that binds to an epitope within or overlapping amino acids 420-430 of SEQ ID NO:1.

In another aspect, the present disclosure provides nucleic acids encoding an anti-FAAH2 antibody. In some embodiments, nucleic acids encode an antibody that binds to an epitope within a C-terminal region of an FAAH2, e.g., an epitope located C-terminal of the amidase signature domain, e.g., C-terminal of ~ amino acid 246 of SEQ ID NO:1. In some embodiments, nucleic acids encode an antibody that binds to an epitope within or overlapping amino acids 246-532 of SEQ ID NO:1 (e.g., an epitope within or overlapping amino acids 246-437, 284-437, 300-437, 330-437, 360-437, 390-437, 330-532, 360-532, 390-532, 330-489, 330-476, 330-446, or 414-437 of SEQ ID NO:1). In some embodiments, nucleic acids encode an antibody that binds to an epitope within or overlapping amino acids 414-437 of SEQ ID NO:1 (i.e., an epitope within or overlapping the following amino acid sequence: LEEKLRYSNEKYQKFKAVEESLRK (SEQ ID NO:3)). In some embodiments, nucleic acids encode an antibody that binds to an epitope within or overlapping amino acids 414-430 of SEQ ID NO:1. In some embodiments, nucleic acids encode an antibody that binds to an epitope within or overlapping amino acids 414-425 of SEQ ID NO:1. In some embodiments, nucleic acids encode an antibody that binds to an epitope within or overlapping amino acids 420-430 of SEQ ID NO:1. Also provided are expression vectors that include the nucleic acids; and host cells that express anti-FAAH2 antibodies.

In still another aspect, the present disclosure provides a method of evaluating a sample for the presence of FAAH2. The method includes, for example, contacting a sample with an antibody that specifically binds to FAAH2 (e.g., wherein the antibody binds to an epitope within or overlapping amino acids 414-437 of SEQ ID NO:1); and determining whether the antibody specifically binds to a polypeptide in the sample, wherein specific binding of the antibody to a polypeptide in the sample indicates that FAAH2 is present in the sample. In some embodiments, the method includes comparison to one or more controls (e.g., comparison to a sample known to include FAAH2). In some embodiments, the method includes comparison of FAAH2 expression to expression of a second polypeptide, such as FAAH1. The sample can be a biological sample from a subject (e.g., a cell, tissue, or fluid such as a blood sample). In some embodiments, the sample is a blood or blood-derived sample. In some embodiments, the sample is a from a tissue (e.g., heart). In some embodiments, the antibody is labeled. The method can include one or more of ELISA, Western blot, immunoprecipitation, and immunohistochemistry.

In another aspect, the present disclosure provides a method of modulating FAAH2 activity in a sample. The method includes contacting a sample with an antibody that modulates a biological activity of the FAAH2 (e.g., wherein the antibody binds to an epitope within or overlapping amino acids 414-437 of SEQ ID NO:1), and wherein the antibody exhibits one or both of the following activities: (a) modulating (e.g., inhibiting) FAAH2 binding to a FAAH2 ligand, and (b) modulating (e.g., inhibiting) fatty acid amide hydrolase activity of FAAH2.

In another aspect, the present disclosure provides a method of purifying FAAH2 from a sample. The method includes contacting a sample that includes FAAH2 with an antibody that specifically binds to FAAH2 (e.g., wherein the antibody binds to an epitope within or overlapping amino acids 414-437 of SEQ ID NO:1); and isolating FAAH2 bound to the antibody, thereby purifying FAAH2 from the sample. The sample containing FAAH2 bound to the anti-FAAH2 antibody can be washed prior to isolating the FAAH2. In some embodiments, the anti-FAAH2 antibody is bound to a solid support.

In another aspect, the present disclosure provides a method of producing an anti-FAAH2 antibody. The method includes immunizing an animal (e.g., a rabbit, mouse, hamster, guinea pig, rat, goat, chicken, sheep, or horse) with a peptide comprising an epitope of FAAH2 (e.g., an epitope within a C-terminal region of an FAAH2, e.g., an epitope located C-terminal of the amidase signature domain, e.g., C-terminal of ~ amino acid 246 of SEQ ID NO:1, e.g., an epitope within or overlapping amino acids 246-532 of SEQ ID NO:1, an epitope within or overlapping amino acids 246-437, 284-437, 300-437, 330-437, 360-437, 390-437, 330-532, 360-532, 390-532, 330-489, 330-476, 330-446, or 414-437 of SEQ ID NO:1); and isolating an antibody from the animal. The peptide can include a fragment of FAAH2, e.g., a fragment which overlaps amino acids 414-437 of SEQ ID NO:1. In some embodiments, the peptide is 8-100 amino acids in length (e.g., 8-50, 8-30, or 8-24 amino acids in length). In some embodiments, the peptide includes at least 8, 9, 10, 11, 12, 13, 14, 15, 16, 17, 18, 19, 20, 21, 22, 23, or 24 amino acids of the following amino acid sequence: LEEKLRYSNEKYQKFKAVEESLRK (SEQ ID NO:3). The peptide can further include one or more heterologous (i.e., non-FAAH2) amino acid residues (e.g., an N-terminal cysteine). In some embodiments, the peptide is linked to a carrier protein (e.g., Keyhole limpet hemocyanin or bovine serum albumin).

In another aspect, the present disclosure provides a method of producing a hybridoma that expresses an anti-FAAH2 antibody. The method includes immunizing an animal with a peptide comprising an epitope of FAAH2 (e.g., an epitope from the C-terminal region of an FAAH2, e.g., an epitope within or overlapping amino acids 414-437 of SEQ ID NO:1); fusing spleen cells from the immunized animal with cells of an immortalized cell line (e.g., myeloma cells) to produce a hybridoma.

In another aspect, the present disclosure provides a peptide consisting of an amino acid sequence at least 90% identical to the following amino acid sequence: LEEKLRYSNEKYQKFKAVEESLRK (SEQ ID NO:3). In some embodiments, the peptide consists of the amino acid sequence of SEQ ID NO:3. Also provided are immunogenic compositions including the peptide.

In another aspect, the present disclosure provides a peptide including at least 8, 9, 10, 11, 12, 13, 14, 15, 16, 17, 18, 19, 20, 21, 22, 23, or 24 amino acids of the following sequence: LEEKLRYSNEKYQKFKAVEESLRK (SEQ ID NO:3), wherein the peptide is 8-200, 8-150, 8-100, 8-75, 8-50, 8-30, or 8-24 amino acids in length. In some embodiments, the peptide comprises a fragment of SEQ ID NO:1. Also provided are immunogenic compositions including the peptide.

The details of one or more embodiments of the present disclosure are set forth in the description below. Other features, objects, and advantages of the present disclosure will be apparent from the description and from the claims. All cited patents, and patent applications and references (including references to public sequence database entries) are incorporated by reference in their entireties for all purposes.

DEFINITIONS

Antibody: The term "antibody" as used herein refers to an intact antibody or an antigen binding fragment (i.e., "antigen-binding portion") or single chain (i.e., light or heavy chain) thereof. An intact antibody is a glycoprotein comprising at least two heavy (H) chains and two light (L) chains interconnected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antigen binding portion: The term "antigen binding portion" of an antibody, as used herein, refers to one or more fragments of an intact antibody that retain the ability to specifically bind to a given antigen (e.g., FAAH2). Antigen binding functions of an antibody can be performed by fragments of an intact antibody. Examples of binding fragments encompassed within the term "antigen binding portion" of an antibody include a Fab fragment, a monovalent fragment consisting of the $V_L$, $V_H$, $C_L$ and CH1 domains; an F(ab)$_2$ fragment, a bivalent fragment comprising two Fab fragments (generally one from a heavy chain and one from a light chain) linked by a disulfide bridge at the hinge region; an Fd fragment consisting of the $V_H$ and CH1 domains; an Fv fragment consisting of the $V_L$ and $V_H$ domains of a single arm of an antibody; a single domain antibody (dAb) fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by an artificial peptide linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more "antigen binding portions" of an antibody. These antibody fragments are obtained using conventional techniques known to those of skill in the art, and the fragments are screened for utility in the same manner as are intact antibodies.

Antigen binding portions can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding portions can be incorporated into single chain molecules comprising a pair of tandem Fv segments ($V_H$—CH1-$V_H$—CH1) which, together with complementary light chain polypeptides, form a pair of antigen binding regions (Zapata et al., 1995 Protein Eng. 8(10):1057-1062; and U.S. Pat. No. 5,641,870).

Cross react: An antibody that "cross-reacts with an antigen" is intended to refer to an antibody that binds that antigen with a $K_D$ of $1\times10^{-6}$ M or less. An antibody that "does not cross-react" with a given antigen is intended to refer to an antibody that either does not bind detectably to the given antigen, or binds with a $K_D$ of $1\times10^{-5}$ M or greater. In certain embodiments, such antibodies that do not cross-react with the antigen exhibit essentially undetectable binding against these antigens in standard binding assays.

High affinity: As used herein, the term "high affinity", when referring to an IgG antibody, indicates that the antibody has a $K_D$ of $10^{-9}$ M or less for a target antigen (e.g., FAAH2).

Human antibody: As used herein, the term "human antibody", includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. Human antibodies may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Human monoclonal antibody: The term "human monoclonal antibody" refers to an antibody displaying a single binding specificity that has variable regions in which both the framework and CDR regions are derived from human sequences. In one embodiment, a human monoclonal antibody is produced by a hybridoma that includes a B cell obtained from a transgenic nonhuman animal (e.g., a transgenic mouse having a genome comprising a human heavy chain transgene and a light chain transgene) fused to an immortalized cell.

Isolated antibody: An "isolated anti-FAAH2 antibody", as used herein, refers to an antibody that is substantially free of molecules having antigenic specificities for antigens other than FAAH2 (e.g., an isolated antibody that specifically binds human FAAH2 is substantially free of antibodies that specifically bind antigens other than human FAAH2). An isolated anti-FAAH2 antibody may, however, have cross-reactivity to other antigens, such as FAAH2 from other species. An antibody is "purified" if it is substantially free of cellular material.

Isotype: As used herein to refer to an antibody, "isotype" refers to the antibody class or subclass (e.g., IgM, IgA, IgE, IgG such as IgG1 or IgG4) that is encoded by the heavy chain constant region gene.

Monoclonal antibody composition: The term "monoclonal antibody composition" as used herein refers to a preparation of antibody molecules of single molecular composition. A monoclonal antibody composition displays a single binding specificity and affinity for a particular epitope.

Polypeptide: The term "polypeptide", as used herein, generally has its art-recognized meaning of a polymer of at least three amino acids. Those of ordinary skill in the art will appreciate, however, that the term "polypeptide" is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Other regions of similarity and/or identity can be determined by those of ordinary skill in the art by analysis of the sequences of various polypeptides.

Sample: The term "sample" is used herein in its broadest sense. A sample (e.g., a biological sample) may be obtained from a cell line or a subject (e.g., a human) or from components (e.g., tissues) of a subject. A biological sample may be of any biological tissue or fluid. Samples include, but are not limited to, bodily fluids which may or may not contain cells, e.g., blood, urine, synovial fluid, saliva, and joint fluid; tissue or fine needle biopsy samples, such as from bone or cartilage; and archival samples with known diagnosis, treatment and/or outcome history. Biological samples may also include sections of tissues such as frozen sections taken from histological purposes. The term sample also encompasses any material derived by processing the sample. Derived materials include, but are not limited to, cells (or their progeny) isolated from the sample, proteins or nucleic acid molecules extracted from the sample. Processing of the sample may involve one or more of: filtration, distillation, extraction, concentration, inactivation of interfering components, addition of reagents, and the like.

Specifically binds: As used herein, an anti-FAAH2 antibody that "specifically binds to FAAH2" is intended to refer to an antibody that binds to an FAAH2 polypeptide with a $K_D$ of $1\times10^{-7}$ M or less. The phrases "an antibody recognizing an antigen" and "an antibody specific for an antigen" are used interchangeably herein with the term "an antibody that specifically binds to an antigen."

Test sample: As used herein, a "test sample" refers to a biological sample obtained from a subject of interest, including a biological fluid (e.g., serum), cell sample, or tissue.

DETAILED DESCRIPTION OF CERTAIN EMBODIMENTS OF THE INVENTION

The present disclosure provides immunogenic epitopes of FAAH2 as well as antibodies that specifically bind FAAH2 and are useful in the detection and isolation of the enzyme, among other applications. FAAH2 has 20% sequence identity to FAAH1 and has a distinct tissue expression pattern and substrate specificity. FAAH2 belongs to the amidase signature family, members of which possess a Lys-Ser-Ser catalytic triad. FAAH2 is ~60 kDa, and includes a transmembrane domain. The C-terminal catalytic domain is thought to be oriented toward the luminal side of the endoplasmic reticulum. FAAH2 mRNA is expressed in the heart, and at lower levels in the brain, testes, and intestines. FAAH2 may regulate endocannabinoid levels in the heart. The FAAH2 gene is located on the X-chromosome. Rats and mice express FAAH1 but do not express FAAH2.

Exemplary amino acid and nucleotide sequences of human FAAH2 are shown in Table 1. The N-terminal transmembrane domain is located between residues 9-25 of the human amino acid sequence. The amidase signature is located between residues 123-246 of the human amino acid sequence.

TABLE 1

Exemplary FAAH2 Amino Acid and Polypeptide Sequences

| Name (species) | GenBank GI No. Accession No. | Sequence |
|---|---|---|
| fatty acid amide hydrolase 2 amino acid sequence (Homo sapiens) | GI: 195972892 NP_777572.2 | MAPSFTARIQLFLLRALGFLIGLVGRAALVLGGPKFASKTPRPV TEPLLLLSGMQLAKLIRQRKVKCIDVVQAYINRIKDVNPMINGI VKYRFEEAMKEAHAVDQKLAEKQEDEATLENKWPFLGVPLTVKE AFQLQGMPNSSGLMNRRDAIAKTDATVVALLKGAGAIPLGITNC SELCMWYESSNKIYGRSNNPYDLQHIVGGSSGGEGCTLAAACSV IGVGSDIGGSIRMPAFFNGIFGHKPSPGVVPNKGQFPLAVGAQE LFLCTGPMCRYAEDLAPMLKVMAGPGIKRLKLDTKVHLKDLKFY WMEHDGGSFLMSKVDQDLIMTQKKVVVHLETILGASVQHVKLKK MKYSFQLWIAMMSAKGHDGKEPVKFVDLLGDHGKHVSPLWELIK WCLGLSVYTIPSIGLALLEEKLRYSNEKYQKFKAVEESLRKELV DMLGDDGVFLYPSHPTVAPKHHVPLTRPFNFAYTGVFSALGLPV TQCPLGLNAKGLPLGIQVVAGPFNDHLTLAVAQYLEKTFGGWVC PGKF (SEQ ID NO: 1) |
| fatty acid amide hydrolase 2 nucleotide sequence (Homo sapiens) | GI: 195972891 NM_174912.3 | GATAAACAAGCTCCTGTGGAATTGTGGGTAGACACTGGACTTGT AAACGAAAAGCTTCATAAGTCCCTCTTTGCTTAGTACTTTTCTC GTCCTTTCCCCAGGGTGCACGTAACCCTCAAGCACTAGGACCGT GCGGAATCCAGGCTGCGATGGCACCTTCATTTACCGCCCGCATT CAGTTGTTCCTCTTGCGGGCGCTAGGCTTTCTCATAGGCTTAGT AGGCCGAGCAGCTTTAGTCTTAGGGGGTCCAAAGTTTGCCTCAA AGACCCCTCGGCCGGTGACTGAACCATTGCTTCTGCTTTCGGGG ATGCAGCTGGCCAAGCTGATCCGACAGAGAAAGGTGAAATGTAT AGATGTTGTTCAGGCTTATATCAACAGAATCAAGGACGTGAACC CAATGATCAATGGAATTGTCAAGTACAGGTTTGAGGAAGCGATG AAGGAGGCTCATGCTGTAGATCAAAAGCTTGCAGAGAAGCAGGA AGATGAAGCCACCCTGGAAAATAAATGGCCCTTCCTTGGGGTTC |

TABLE 1-continued

Exemplary FAAH2 Amino Acid and Polypeptide Sequences

| Name (species) | GenBank GI No. Accession No. | Sequence |
|---|---|---|
| | | CTTTGACAGTCAAGGAAGCTTTCCAGCTACAAGGAATGCCCAAT<br>TCTTCTGGACTCATGAACCGTCGTGATGCCATTGCCAAAACAGA<br>TGCCACTGTGGTGGCATTACTGAAGGGAGCTGGTGCCATTCCTC<br>TTGGCATAACCAACTGTAGTGAGTTGTGTATGTGGTATGAATCC<br>AGTAACAAGATCTATGGCCGATCAAACAACCCATATGATTTACA<br>GCATATTGTAGGTGGAAGTTCTGGTGGTGAGGGCTGCACACTGG<br>CAGCTGCCTGCTCAGTTATTGGTGTGGGCTCTGATATTGGTGGT<br>AGCATTCGAATGCCTGCTTTCTTCAATGGTATATTTGGACACAA<br>GCCTTCTCCAGGTGTGGTTCCCAACAAAGGTCAGTTTCCCTTGG<br>CTGTGGGAGCCCAGGAGTTGTTTCTGTGCACTGGTCCTATGTGC<br>CGTTATGCTGAAGACCTGGCCCCCATGTTGAAGGTCATGGCAGG<br>ACCTGGGATCAAAAGGTTAAAACTAGACACAAAGGTACATTTAA<br>AAGACTTAAAATTTTACTGGATGGAACATGATGGAGGCTCATTT<br>TTAATGTCCAAAGTGGACCAAGATCTCATTATGACTCAGAAAAA<br>GGTTGTGGTTCACCTTGAAACTATTCTAGGAGCCTCAGTTCAAC<br>ATGTTAAACTGAAGAAAATGAAGTACTCTTTTCAGTTGTGGATC<br>GCAATGATGTCAGCAAAGGGACATGATGGGAAGGAACCTGTGAA<br>ATTTGTAGATTTGCTTGGTGACCATGGGAAACATGTCAGTCCTC<br>TGTGGGAGTTGATCAAATGGTGCCTGGGTCTGTCAGTGTACACC<br>ATCCCTTCCATTGGACTGGCTTTGTTGGAAGAAAAGCTCAGATA<br>TAGCAATGAGAAATACCAAAAGTTTAAGGCAGTGGAAGAAAGCC<br>TGCGTAAAGAGCTGGTGGATATGCTAGGTGATGATGGTGTGTTC<br>TTATATCCCTCACATCCCACAGTGGCACCTAAGCATCATGTCCC<br>TCTAACACGGCCTTTCAACTTTGCTTACACAGGTGTCTTCAGTG<br>CCCTGGGTTTGCCTGTGACCCAATGCCCACTGGGACTGAATGCC<br>AAAGGACTCCCTTTAGGCATCCAGGTTGTGGCTGGACCCTTTAA<br>TGATCATCTGACCCTGGCTGTGGCCCAGTACTTGGAGAAAACTT<br>TTGGGGGCTGGGTCTGTCCAGGAAAGTTTTAGGAGGACCTTCTG<br>CAAGGTTAATGTGTGTGTGTTTGTGTTCGTGTGGTGGTGTTT<br>CTATTAATTGGGTGAAATCAAGCACCAGCAGACAAGCAGAGAAA<br>CAACTGGGGAATTTATTGACTCATTTAGTTATTCTTTCTACTTT<br>TATTTCCTTCTCTAACTGTTGGTCTTACTAAAATGGTAATATTT<br>GCTTCTTGCTTTTATGTTACTGGAAAATTAGGACATGTAAATGG<br>ATAAGTGCAATAAAGTTTCCTAAATGCTGGAAAAAAAAAAAAAA<br>AAAAAAAAAAAAAA (SEQ ID NO: 2) |

A predicted amino acid sequence of FAAH2 from macaques (*Macaca mulatta*) is found in GenBank under Acc. No. XP_001095907.1, GI:109130979. A predicted amino acid sequence for opossum (*Monodelphis domestica*) FAAH2 is found in GenBank under Acc. No. XP_001375446.1, GI:126342021. An amino acid sequence for zebrafish (*Danio rerio*) FAAH2 is found in GenBank under Acc. No. NP_001002700.1, GI:50540464.

Antigenic epitopes of human FAAH2 are provided herein. In some embodiments, an antigenic epitope is an epitope within a C-terminal region of an FAAH2, e.g., an epitope located C-terminal of the amidase signature domain, e.g., C-terminal of amino acid 246 of SEQ ID NO:1. In some embodiments, an antigenic epitope is within or overlapping amino acids 246-532 of SEQ ID NO:1 (e.g., an epitope within or overlapping amino acids 246-437, 284-437, 300-437, 330-437, 360-437, 390-437, 330-532, 360-532, 390-532, 330-489, 330-476, 330-446, or 414-437 of SEQ ID NO:1).

An antigenic epitope of human FAAH2 can include the following sequence, corresponding to amino acids 414-437 of SEQ ID NO:1: LEEKLRYSNEKYQKFKAVEESLRK (SEQ ID NO:3), an overlapping sequence, a sequence having 1, 2, 3, 4, 5, or 6 amino acid substitutions, or a portion thereof. Examples of overlapping epitopes include, for example, peptides corresponding to amino acids 400-424, 405-429, 410-434, 420-444, 425-449, and 430-454 of SEQ ID NO:1. Overlapping sequences that have fewer (e.g., 8-23) or more (e.g., 25-75) residues are also contemplated. Examples of portions include peptides having at least 8, 9, 10, 11, 12, 13, 14, 15, 16, 17, 18, 19, 20, 21, 22, or 23 contiguous amino acids of SEQ ID NO:3.

Epitopes of FAAH2 from FAAH2 sequences of non-human species are also provided. Such epitopes can include, for example, an epitope in a C-terminal region, e.g., an epitope found at a position in the non-human sequence that aligns to amino acids 414-437 of SEQ ID NO:1. Overlapping sequences, sequences having 1, 2, 3, 4, 5, or 6 amino acid substitutions, and portions thereof of such non-human FAAH2 polypeptides are also provided.

Peptides including antigenic epitopes can be prepared and used to immunize animals to produce antibodies. In certain embodiments, a peptide is linked to a heterologous amino acid or a heterologous peptide sequence (e.g., to a tag, to a carrier polypeptide and/or to insert an amino acid residue to facilitate coupling to a carrier polypeptide). In some embodiments, an antigenic epitope includes the following sequence:

CLEEKLRYSNEKYQKFKAVEESLRK. (SEQ ID NO: 4)

Anti-FAAH2 Antibodies

The present disclosure provides antibodies that specifically bind to FAAH2. In some embodiments, an antibody binds to an epitope within a C-terminal region of an FAAH2, e.g., an epitope located C-terminal of the amidase signature domain, e.g., C-terminal of ~ amino acid 246 of SEQ ID NO:1. In some embodiments, an antibody binds to an epitope within or overlapping amino acids 246-532 of SEQ ID NO:1 (e.g., an epitope within or overlapping amino acids 246-437, 284-437, 300-437, 330-437, 360-437, 390-437, 330-532, 360-532, 390-532, 330-489, 330-476, 330-446, or 414-437 of SEQ ID NO:1). In some embodiments, an antibody binds to an epitope within or overlapping amino acids 414-437 of SEQ ID NO:1 (i.e., an epitope within or overlapping the following amino acid sequence: LEEKLRYSNEKYQK-FKAVEESLRK (SEQ ID NO:3)). In some embodiments, an antibody binds to an epitope within or overlapping amino acids 414-430 of SEQ ID NO:1. In some embodiments, an antibody binds to an epitope within or overlapping amino acids 414-425 of SEQ ID NO:1. In some embodiments, an antibody binds to an epitope within or overlapping amino acids 420-430 of SEQ ID NO:1. In some embodiments, an anti-FAAH2 antibody is a polyclonal antibody. In some embodiments, an anti-FAAH2 antibody is a monoclonal antibody. Anti-FAAH2 antibodies provided herein include high affinity antibodies that do not cross react with FAAH1.

An anti-FAAH2 antibody can be a fully human antibody (e.g., an antibody made in a mouse which has been genetically engineered to produce an antibody from a human immunoglobulin sequence), or a non-human antibody, e.g., a mouse, rat, guinea pig, hamster, goat, primate (e.g., monkey), sheep, horse, chicken, or camel antibody.

In some embodiments, an anti-FAAH2 antibody is an engineered and/or modified anti-FAAH2 antibody. An anti-FAAH2 antibody can be prepared using an antibody having one or more $V_H$ and/or $V_L$ sequences as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., 1998 Nature 332:323-327; Jones et al., 1986 Nature 321:522-525; Queen et al., 1989 Proc. Natl. Acad. See. U.S.A. 86:10029-10033; U.S. Pat. No. 5,225,539, and U.S. Pat. Nos. 5,530,101; 5,585,089; 5,693,762 and 6,180,370).

Framework sequences can be obtained from public DNA databases or published references that include germline antibody gene sequences. For example, germline DNA sequences for human heavy and light chain variable region genes can be found in the "VBase" human germline sequence database (available on the internet at mrc-cpe.cam.ac.uk/vbase), as well as in Kabat et al., 1991 Sequences of Proteins of Immunological Interest, Fifth Edition, U.S. Department of Health and Human Services, NIH Publication No. 91-3242; Tomlinson et al., 1992 J. Mol. Biol. 227:776-798; and Cox et al., 1994 Eur. J. Immunol. 24:827-836.

The $V_H$ CDR1, 2 and 3 sequences and the $V_L$ CDR1, 2 and 3 sequences can be grafted onto framework regions that have the identical sequence as that found in the germline immunoglobulin gene from which the framework sequence is derived, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

CDRs can also be grafted into framework regions of polypeptides other than immunoglobulin domains. Appropriate scaffolds form a conformationally stable framework that displays the grafted residues such that they form a localized surface and bind the target of interest (e.g., FAAH2). For example, CDRs can be grafted onto a scaffold in which the framework regions are based on fibronectin, ankyrin, lipocalin, neocarzinostain, cytochrome b, CP1 zinc finger, PST1, coiled coil, LACI-D1, Z domain or tendramisat (See e.g., Nygren and Uhlen, 1997 Current Opinion in Structural Biology, 7, 463-469).

Another type of variable region modification is mutation of amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s), and the effect on antibody binding, or other functional property of interest, can be evaluated in in vitro or in vivo assays as described herein. Conservative modifications can be introduced. The mutations may be amino acid substitutions, additions or deletions. Moreover, typically no more than one, two, three, four or five residues within a CDR region are altered.

Engineered anti-FAAH2 antibodies provided herein include those in which modifications have been made to framework residues within $V_H$ and/or $V_L$, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Pat. Pub. No. 20030153043 by Can et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an anti-FAAH2 antibody may be chemically modified (e.g., one or more chemical moieties can be attached to the antibody) or be modified to alter its glycosylation, again to alter one or more functional properties of the antibody.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, U.S. Pat. No. 6,277,375 describes the following mutations in an IgG that increase its half-life in vivo: T252L, T254S, T256F. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in WO 00/42072 by Presta. Moreover, the binding sites on human IgG1 for FcγR1, FcγRII, FcγRIII and FcRn have been mapped and variants with improved binding have been described (see Shields, R. L. et al., 2001 J. Biol. Chem. 276:6591-6604).

In still another embodiment, the glycosylation of an antibody is modified. For example, an aglycoslated antibody can be made (i.e., the antibody lacks glycosylation). Glycosylation can be altered, for example, to increase the affinity of the antibody for an antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

An anti-FAAH2 antibody can be labeled, e.g., with a detectable substance. Examples of detectable substances include enzymes, prosthetic groups, fluorescent materials, luminescent materials, bioluminescent materials, and radioactive materials. Examples of enzymes include horseradish peroxidase, alkaline phosphatase, β-galactosidase, or acetylcholinesterase; examples of prosthetic group complexes include streptavidin/biotin and avidin/biotin; examples of fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of radioactive material include $^{125}I$, $^{131}I$, $^{35}S$ or $^{3}H$.

Monoclonal Antibody Generation

Monoclonal antibodies (mAbs) can be produced by a variety of techniques, including conventional monoclonal antibody methodology e.g., the standard somatic cell hybridization technique of Kohler and Milstein (Nature, 256:495, 1975), or using library display methods, such as phage display.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known. Chimeric or humanized antibodies to FAAH2 can be prepared based on the sequence of a murine monoclonal antibody prepared as described herein. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539, and U.S. Pat. Nos. 5,530,101; 5,585,089; 5,693,762 and 6,180,370.

In a certain embodiment, anti-FAAH2 antibodies are human monoclonal antibodies. Such human monoclonal antibodies directed against FAAH2 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see, e.g., Lonberg et al., Nature 368(6474): 856-859, 1994). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., Intern. Rev. Immunol. 13: 65-93, 1995; and Harding, F. and Lonberg, N., Ann. N. Y. Acad. Sci. 764:536-546, 1995). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Pub. Nos. WO 92103918, WO 93/12227, WO 94/25585, WO 97113852, WO 98/24884 and WO 99/45962, all to Lonberg and Kay; and PCT Pub. No. WO 01/14424 to Korman et al.

In another embodiment, human antibodies against FAAH2 can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in WO 02/43478.

Still further, alternative transgenic animal systems expressing human immunoglobulin genes are available in the art and can be used to raise anti-FAAH2 antibodies. For example, an alternative transgenic system referred to as the Xenomouse® (Abgenix, Inc.) can be used. Such mice are described in, e.g., U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-FAAH2 antibodies. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-FAAH2 antibodies.

Human monoclonal antibodies can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Libraries can be screened for binding to full length FAAH2 or to a particular epitope of FAAH2.

Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Nucleic Acid Molecules Encoding Anti-FAAH2 Antibodies

Another aspect of the present disclosure pertains to nucleic acid molecules that encode anti-FAAH2 antibodies. The nucleic acids may be present in whole cells, in a cell lysate, or may be nucleic acids in a partially purified or substantially pure form. A nucleic acid can be, for example, DNA or RNA and may or may not contain intronic sequences. In an embodiment, the nucleic acid is a cDNA molecule. A nucleic acid may be present in a vector such as a phage display vector, or in a recombinant plasmid vector.

Nucleic acids can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

An isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. A heavy chain constant region can be an IgG1, IgG2, IgG3, IgG4, IgA, IgE, IgM or IgD constant region. For a Fab fragment heavy chain gene, the $V_H$-encoding DNA can be operatively linked to another DNA molecule encoding only the heavy chain CH1 constant region.

An isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et al., 1988 Proc. Natl. Acad. Sci. USA 85:5879-5883; McCafferty et al., 1990 Nature 348:552-554).

Anti-FAAH2 antibodies can be produced in a host cell transfectoma using, for example, a combination of recombinant DNA techniques and gene transfection methods as is well known in the art (e.g., Morrison, 1985 Science 229: 1202). For example, to express antibodies, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. Expression vector and expression control sequences are chosen to be compatible with the expression host cell used. An antibody light chain gene and antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, recombinant expression vectors carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. 1990 Methods in Enzymology 185, Academic Press, San Diego, Calif.). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe et al., 1988 Mol. Cell. Biol. 8:466-472).

In addition to the antibody chain genes and regulatory sequences, recombinant expression vectors may carry additional sequences, such as sequences that regulate replication of the vector in host cells (e.g., origins of replication) and selectable marker genes. A selectable marker gene facilitates selection of host cells into which the vector has been introduced (see, e.g., U.S. Pat. Nos. 4,399,216; 4,634,665; and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is possible to express antibodies in either prokaryotic or eukaryotic host cells. Eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood, 1985 Immunology Today 6:12-13).

Mammalian host cells for expressing the recombinant anti-FAAH2 antibodies include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in Kaufman and Sharp, 1982 Mol. Biol. 159:601-621, NSO myeloma cells, COS cells and SP2 cells. In particular, for use with NSO myeloma cells, another expression system is the GS gene expression system shown in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Applications

Anti-FAAH2 antibodies can be used to isolate FAAH2 by standard techniques, such as affinity chromatography or immunoprecipitation. Anti-FAAH2 antibodies described herein can be used in methods of detecting FAAH2 in a sample. In some embodiments, an anti-FAAH2 antibody is used in a diagnostic or prognostic assay.

In various embodiments, the presence, level, or absence of a FAAH2 polypeptide expression in a biological sample can be evaluated by obtaining a biological sample from a subject and contacting the biological sample with an anti-FAAH2 antibody. A variety of techniques can be used to determine the presence, level, or absence of an FAAH2 polypeptide. In some embodiments, an anti-FAAH2 antibody bears a detectable label. Labeled antibodies include antibodies that are directly labeled with a detectable substance (e.g., by physically linking the label), as well as indirectly labeled antibodies.

In vitro techniques for detection of FAAH2 include enzyme linked immunosorbent assays (ELISAs), immunoprecipitations, immunofluorescence, immunohistochemical methods, enzyme immunoassay (EIA), radioimmunoassay (RIA), and Western blot analysis. In vivo techniques for detection include introducing into a subject a labeled anti-FAAH2 antibody, e.g., wherein the antibody is labeled with a fluorescent or radioactive label, or another type of label detectable by standard imaging techniques. In another embodiment, the sample is labeled, e.g., biotinylated and then contacted to the antibody, e.g., an anti-FAAH2 antibody. The sample can be detected, e.g., with avidin coupled to a fluorescent label.

In some embodiments, methods of detecting FAAH2 further include contacting a control sample with an anti-FAAH2 antibody, and comparing the presence of FAAH2 in the control sample with the presence of FAAH2 protein in the test sample.

In some embodiments, methods of detecting FAAH2 further include contacting a sample with a peptide fragment of FAAH2 (e.g., a peptide fragment comprising all or a portion of the sequence of SEQ ID NO:3) in the presence of an anti-FAAH2 antibody, to determine whether the peptide competes for binding to the antibody, thereby allowing confirmation of specificity of an antigen-antibody interaction. In some embodiments, the peptide fragment is the peptide fragment used to generate the anti-FAAH2 antibody.

The present disclosure also provides kits for detecting the presence, level, or absence of FAAH2 in a sample. A kit can include an anti-FAAH2 antibody described herein. In some embodiments, a kit further includes a standard. The anti-FAAH2 antibody can be packaged in a suitable container. In some embodiments, a kit includes: (1) a first antibody (e.g., attached to a solid support) which binds to FAAH2, (2) a second, different antibody which binds to either the FAAH2 or the first antibody and is conjugated to a detectable agent. In some embodiments, a kit includes a buffering agent, a preservative, or a protein stabilizing agent. A kit can also include components necessary for detecting the detectable agent (e.g., an enzyme or a substrate). A kit can also contain a control sample or a series of control samples which can be assayed and compared to a test sample. Each component of a kit can be enclosed within an individual container and all of the various containers can be within a single package, along with instructions for interpreting the results of the assays performed using the kit.

In some embodiments, an anti-FAAH2 antibody is used in a diagnostic methods, e.g., to identify subjects having, or at risk of developing, a disease or disorder associated with misexpressed or aberrant or unwanted FAAH2 expression or activity. In some embodiments, the disease or disorder is heart condition (e.g., myocardial injury, ischemia, and/or infarction).

In some embodiments, a disease or disorder associated with aberrant or unwanted FAAH2 expression or activity is identified. A test sample is obtained from a subject and FAAH2 polypeptide expression is evaluated, wherein the level, e.g., the presence or absence, of FAAH2 polypeptide is diagnostic for a subject having or at risk of developing a disease or disorder associated with aberrant or unwanted FAAH2 expression or activity. In some embodiments, an assay described herein is used to determine whether a subject can be administered an agent to treat a disease or disorder associated with aberrant or unwanted FAAH2 expression or activity.

In some embodiments, FAAH2 expression or activity is a marker of a disorder or disease state and/or as a marker for a precursor or predisposition of a disease state, as a marker of drug activity, or as a marker of a pharmacogenomic profile of a subject. The presence, absence and/or quantity of FAAH2 in a subject or sample from a subject can be detected using an anti-FAAH2 antibody described herein and may be correlated with one or more biological states in vivo. For example, FAAH2 may serve as a surrogate marker (i.e., an objective biochemical marker which correlates with the absence or presence of a disease or disorder, or with the progression of a disease or disorder, e.g., a cardiovascular disorder) for one or more disorders or disease states or for conditions leading up to disease states (e.g., cardiovascular disease states). The presence or quantity of a surrogate marker is independent of the disease. Therefore, a marker may serve to indicate whether a particular course of treatment is effective in lessening a disease state or disorder. Surrogate markers are of particular use when the presence or extent of a disease state or disorder is difficult to assess through standard methodologies or when an assessment of disease progression is desired before a potentially dangerous clinical endpoint is reached (e.g., an assessment of cardiovascular disease may be made using cholesterol levels as a surrogate marker, well in advance of the undesirable clinical outcomes of myocardial infarction). An examples of the use of surrogate markers is described in Koomen et al., J. Mass. Spectrom. 35: 258-264, 2000.

In some embodiments, FAAH2 is useful as a pharmacodynamic marker (i.e., an objective biochemical marker which correlates specifically with drug effects), and the present disclosure provides methods for evaluating FAAH2 using an anti-FAAH2 antibody described herein. The presence or quantity of a pharmacodynamic marker is not related to the disease state or disorder (e.g., cardiovascular disorder) for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker expression, the amplified marker may be in a quantity which is more readily detectable than the drug itself. Also, the marker may be more easily detected due to the nature of the marker itself for example, using the methods described herein, anti-FAAH2 antibodies may be employed in an immune-based detection system for an FAAH2 marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al., Env. Health Perspect. 90: 229-238, 1991; Schentag, Am. J. Health-Syst. Pharm. 56 Suppl. 3: S21-S24, 1999; and Nicolau, Am, J. Health-Syst. Pharm. 56 Suppl. 3: S16-S20, 1999.

Anti-FAAH2 antibodies described herein can be used in methods of isolating and/or purifying FAAH2 polypeptides. In some embodiments, anti-FAAH2 antibodies are used in methods of identifying molecules that interact with FAAH2 by capturing FAAH2 in a sample and identifying molecules bound to FAAH2 (e.g., naturally occurring binding partners of FAAH2 and/or candidate binding agents).

EXEMPLIFICATION

Example 1

Design of an FAAH2 Antigen

Homology models of human FAAH1 and human FAAH2 were constructed using the published rat FAAH1 protein structure (1mt5) as a template. The sequences were aligned with DeepView/Swiss-PdbViewer software (v3.7) and the homology models were optimized using the Swiss-Prot protein modeling server (available on the internet at the following address: spdbv.vital-it.ch). Residues 414-437 in human FAAH2 aligned with residues 434-457 of both rat FAAH and human FAAH1, were predicted to be exposed on the surface of hFAAH2, and showed only 3 out of 24 amino acids that were identical to human FAAH1 in this region. The sequence was: Leu-Glu-Glu-Lys-Leu-Arg-Tyr-Ser-Asn-Glu-Lys-Tyr-Gln-Lys-Phe-Lys-Ala-Val-Glu-Glu-Ser-Leu-Arg-Lys (SEQ ID NO:3).

Example 2

Generation of FAAH2 Antibodies

An FAAH2 specific antigenic peptide (fh2-peptide) was synthesized via standard solid state peptide synthesis protocols. This peptide had the sequence of the peptide described in Example 1, with the addition of a cysteine residue at the N-terminus to generate a peptide having the following sequence: Cys-Leu-Glu-Glu-Lys-Leu-Arg-Tyr-Ser-Asn-Glu-Lys-Tyr-Gln-Lys-Phe-Lys-Ala-Val-Glu-Glu-Ser-Leu-Arg-Lys (SEQ ID NO:4).

The fh2-peptide was crosslinked to Keyholelimpet hemacyanin (KLH) using maleimide via standard protocols at Pocono Rabbit Farm and Laboratory Inc. (available on the internet at the following web address: prfal.com/protocolforrabbits.php). FAAH2 antibodies were raised by injecting the fh2-peptide solubilized in Complete Freunds Adjuvant. The initial injection with 200 ug peptide was followed by two boost injections of 100 ug two weeks later. Subsequent weekly boost injections with 50 ug of peptide were performed over six weeks.

Antibody (Ab) titers were assayed by ELISA, using the fh2-peptide linked to BSA beads. Rabbit captured FAAH2 antibodies were detected via HRP-conjugated goat anti-rabbit reagent utilizing a chromogenic substrate for quantitation. Once a sufficient titer was achieved, 15 mls of serum was drawn, the serum centrifuged at 10,000 g, and the supernatant diluted 1:1 in Pierce Gentle Binding Buffer. The resulting solution was loaded onto an fh2-peptide affinity column, made with Pierce ultralink affinity column methodology, washed with 1 M NaCl to remove non-specifically bound proteins, and the FAAH2 antibody eluted with Pierce elution buffer. FAAH2 specific antibody protein concentration was determined with a Bio-Rad Bradford reagent. The resulting purified FAAH2 antibody was dialyzed into phosphate buffer saline (PBS) and preserved by the addition of 0.2% Na Azide and 1% BSA. The purified antibody was characterized by an ELISA utilizing the fh2-peptide conjugated to BSA beads, to ensure maintenance of activity after the purification procedure.

Example 3

Characterization of Anti-FAAH2 Antibodies

A plasmid encoding FAAH2 with an N-terminal FLAG tag (hFAAH2/pFLAG-CMV plasmid) was prepared (Wei et al., J. Biol. Chem. 281(48):36569-36578, 2006). To express the polypeptide in Cos7 cells, the cells were transfected at a 30-40% confluency with hFAAH2/pFLAG-CMV with the FuGENE® 6 transfection reagent (Roche Diagnostics, cat. no. 11814 443 001). Cells were harvested after 48 hours via scraping and resuspended in PBS, centrifuged and the pellet snap frozen with liquid nitrogen, and stored at −80° C.

Frozen cell pellets were thawed on ice and resuspended in buffer containing 12.5 mM Hepes (pH 8.0), 100 mM NaCl, and 1 mM EDTA at a ratio of 0.08 g/ml. Cells were lysed via sonication for 10 second periods in triplicate. Cell debris was removed via centrifugation at 1000 g. The resulting supernatant was centrifuged at 13,000 g to pellet cell membrane components (P2). FAAH2, which is present in the P2 pellet, was resolubilized for 1 hour on ice in buffer containing 20 mM Hepes (pH 7.8), 10% v/v glycerol, 1 mM EDTA, and 1% triton X-100, at a ratio of 0.35 mls/gram of original cell pellet. Insoluble debris was removed via centrifugation at 13,000 g, and the supernatant containing FAAH2 was retained for characterization.

Protein concentrations in the P2 supernatant were determined via the BCA protein assay kit (Pierce). P2 supernatant (10 ug) was loaded and run on an SDS gel, transferred to PVDF membrane, and subjected to western blot analysis. The membrane was blocked overnight in blocking solution containing 5% non-fat milk in TBS buffer with Tween (TBST), and subsequently probed for FAAH2 expression via a FLAG M2 antibody (Sigma, F1804) at a 1/1000 dilution in blocking solution for 1 hour at room temperature. After removal of blocking solution, the membrane was washed in TBST and probed with secondary antibody (ECL anti-mouse Ig, HRP conjugated sheep antibody) at a 1/1000 dilution in blocking solution for 1 hour. The membrane was washed and developed with a chemiluminescent reagent. A strong P2 band at the expected molecular weight of 60 kDa was observed, indicating expression of hFAAH2. Antibody-reactive bands were also observed in lanes loaded with cell homogenate, 1000×g supernatant, 1000×g pellet, and 13,000×g supernatant. A FLAG-tag antibody band was not detected in a sample prepared as described above from untransfected cos7 cells.

The human FAAH2-specific antibody generated as described in Example 2 was characterized and compared to the FLAG-tag antibody band. The western blot was stripped via standard protocols, and the membrane probed with rabbit antisera raised to the fh2 peptide (from rabbit 21413; 0.28 mg/ml anti-FAAH2 antibody). At a dilution of 1:25 in blocking buffer. After extensive washing, the membrane was probed with a secondary antibody (ECL donkey HRP conjugated anti rabbit IgG F(ab) fragment) at a 1/1000 dilution in blocking buffer, with a 1 hour incubation. Extensive washing, followed by development with a chemiluminscence reagent indicated an intense band at 60 Kda, which directly overlapped with the FLAG-tagged band. This indicates that the antibody raised to the fh2-peptide specifically recognizes human FAAH2. Other experiments indicated that the antisera did not cross react with human FAAH1.

EQUIVALENTS

Those skilled in the art will recognize, or be able to ascertain using no more than routine experimentation, many equivalents to the specific embodiments of the invention described herein. The scope of the present invention is not intended to be limited to the above Description. Alternative methods and materials and additional applications will be apparent to one of skill in the art, and are intended to be included within the following claims.

We claim:

1. An isolated antibody that specifically binds to a fatty acid amide hydrolase 2 polypeptide (FAAH2), wherein the antibody binds to an epitope within or consisting of amino acids 414-437 of SEQ ID NO:1.

2. The antibody claim 1, wherein the antibody is cross reactive with FAAH2 of a non-human species.

3. The antibody of claim 1, wherein the antibody is not cross-reactive with an FAAH1.

4. The antibody of any of claim 1, wherein the antibody binds to a linear epitope.

5. The antibody of claim 1, wherein the antibody binds to a non-linear epitope.

6. The antibody of claim 1, wherein the antibody binds to the FAAH2 with a dissociation constant ($K_D$) equal to or less than 1 nM.

7. The antibody of claim 6, wherein the antibody binds to the FAAH2 with a $K_D$ equal to or less than 0.5 nM.

8. The antibody of claim 7, wherein the antibody binds to the FAAH2 with a $K_D$ equal to or less than 0.1 nM.

9. The antibody of claim 1, wherein the antibody is a monoclonal antibody.

10. The antibody of claim 1, wherein the antibody is a polyclonal antibody.

11. The antibody of claim 1, wherein the antibody is a human antibody.

12. The antibody of claim 1, wherein the antibody is a humanized antibody.

13. The antibody claim 1, wherein the antibody is an antibody of one of the following isotypes: IgM, IgG, IgA, or IgE.

14. The antibody of claim 1, wherein the antibody modulates FAAH2 binding to an FAAH2 ligand.

15. The antibody of claim 14, wherein the antibody inhibits FAAH2 binding to an FAAH2 ligand.

16. The antibody of claim 14, wherein the antibody modulates FAAH2 binding to a fatty acid.

17. The antibody of claim 16, wherein the antibody inhibits FAAH2 binding to a fatty acid.

18. The antibody of claim 1, wherein the antibody modulates fatty acid amide hydrolase activity of FAAH2.

19. The antibody of claim 18, wherein the antibody inhibits fatty acid amide hydrolase activity of FAAH2.

20. A method of evaluating a sample for the presence of FAAH2, the method comprising:
   contacting a sample with an antibody that specifically binds to FAAH2, wherein the antibody binds to an epitope within or consisting of amino acids 414-437 of SEQ ID NO:1; and
   determining whether the antibody specifically binds to a polypeptide in the sample, wherein specific binding of the antibody to a polypeptide in the sample indicates that FAAH2 is present in the sample.

21. A method of purifying FAAH2 from a sample, the method comprising:
   contacting a sample that includes FAAH2 with an antibody that specifically binds to FAAH2, wherein the antibody binds to an epitope within or consisting of amino acids 414-437 of SEQ ID NO:1; and
   isolating FAAH2 bound to the antibody, thereby purifying FAAH2 from the sample.

* * * * *